(12) United States Patent
Teske et al.

(10) Patent No.: US 7,930,032 B2
(45) Date of Patent: Apr. 19, 2011

(54) ELECTRICAL FEEDTHROUGH

(75) Inventors: Josef Teske, Hallstadt (DE); Stefan Eck, Hoechstadt (DE); Boris Frauenstein, Herzogenaurach (DE); Erich Haas, Flachslanden (DE)

(73) Assignee: Biotronic CRM Patent AG, Baar (CH)

( * ) Notice: Subject to any disclaimer, the term of this patent is extended or adjusted under 35 U.S.C. 154(b) by 37 days.

(21) Appl. No.: 11/781,064

(22) Filed: Jul. 20, 2007

(65) Prior Publication Data

US 2008/0060844 A1   Mar. 13, 2008

(30) Foreign Application Priority Data

Sep. 7, 2006   (DE) .......................... 10 2006 041 940

(51) Int. Cl.
*A61N 1/00* (2006.01)
(52) U.S. Cl. ................... 607/36; 607/32; 607/37
(58) Field of Classification Search .................... 607/32, 607/36–37
See application file for complete search history.

(56) References Cited

U.S. PATENT DOCUMENTS

| | | | | |
|---|---|---|---|---|
| 4,352,951 A * | 10/1982 | Kyle | ...................... | 174/152 GM |
| 4,659,378 A * | 4/1987 | Volz et al. | ........................ | 420/8 |
| 4,816,621 A * | 3/1989 | Huebner et al. | ...... | 174/152 GM |
| 5,406,444 A * | 4/1995 | Selfried et al. | ................ | 361/302 |
| 5,679,026 A * | 10/1997 | Fain et al. | ..................... | 439/651 |
| 5,759,197 A * | 6/1998 | Sawchuk et al. | ................ | 607/36 |
| 5,821,011 A * | 10/1998 | Taylor et al. | ................... | 429/181 |
| 5,942,842 A * | 8/1999 | Fogle, Jr. | ........................ | 313/313 |
| 5,951,595 A * | 9/1999 | Moberg et al. | .................. | 607/37 |
| 6,044,302 A * | 3/2000 | Persuitti et al. | .................. | 607/37 |
| 6,428,368 B1 * | 8/2002 | Hawkins et al. | ............. | 439/271 |
| 6,459,935 B1 * | 10/2002 | Piersma | .......................... | 607/37 |
| 6,519,133 B1 * | 2/2003 | Eck et al. | ...................... | 361/302 |
| 6,529,103 B1 | 3/2003 | Brendel et al. | | |
| 6,566,978 B2 * | 5/2003 | Stevenson et al. | ............. | 333/182 |
| 6,567,259 B2 | 5/2003 | Stevenson et al. | | |
| 6,643,903 B2 | 11/2003 | Stevenson et al. | | |
| 6,765,779 B2 | 7/2004 | Stevenson et al. | | |
| 6,765,780 B2 * | 7/2004 | Brendel et al. | ................ | 361/302 |
| 6,768,629 B1 | 7/2004 | Allen et al. | | |
| 6,822,845 B2 | 11/2004 | Chereson | | |
| 6,852,925 B2 * | 2/2005 | Wolf et al. | .................. | 174/50.6 |
| 6,882,248 B2 * | 4/2005 | Stevenson et al. | ............ | 333/182 |
| 6,934,582 B2 | 8/2005 | Thong et al. | | |

(Continued)

FOREIGN PATENT DOCUMENTS

GB   2127629 A * 4/1984

OTHER PUBLICATIONS

German Search Report, dated May 10, 2007.

*Primary Examiner* — Niketa I Patel
*Assistant Examiner* — Nicole F Lavert
(74) *Attorney, Agent, or Firm* — ARC IP Law, PC; Joseph J. Mayo

(57) ABSTRACT

The present invention relates to an electrical feedthrough for insertion into an opening of an implantable electrical treatment device having an electrically insulating insulation body through which at least one electrically conductive terminal pin passes, which is connected hermetically sealed to the insulation body using a solder, the solder material being glass or glass ceramic.

25 Claims, 13 Drawing Sheets

U.S. PATENT DOCUMENTS

| | | |
|---|---|---|
| 6,987,660 B2 * | 1/2006 | Stevenson et al. ............ 361/302 |
| 6,999,818 B2 | 2/2006 | Stevenson et al. |
| 7,274,963 B2 * | 9/2007 | Spadgenske .................... 607/36 |
| 2002/0027484 A1 * | 3/2002 | Stevenson et al. ............ 333/182 |
| 2003/0139096 A1 * | 7/2003 | Stevenson et al. ............ 439/620 |
| 2004/0012462 A1 * | 1/2004 | Kim ............................... 333/182 |
| 2004/0078062 A1 * | 4/2004 | Spadgenske .................... 607/37 |
| 2004/0116976 A1 * | 6/2004 | Spadgenske .................... 607/37 |
| 2004/0215280 A1 * | 10/2004 | Dublin et al. ................... 607/36 |
| 2008/0314865 A1 * | 12/2008 | Ok et al. ......................... 216/17 |

* cited by examiner

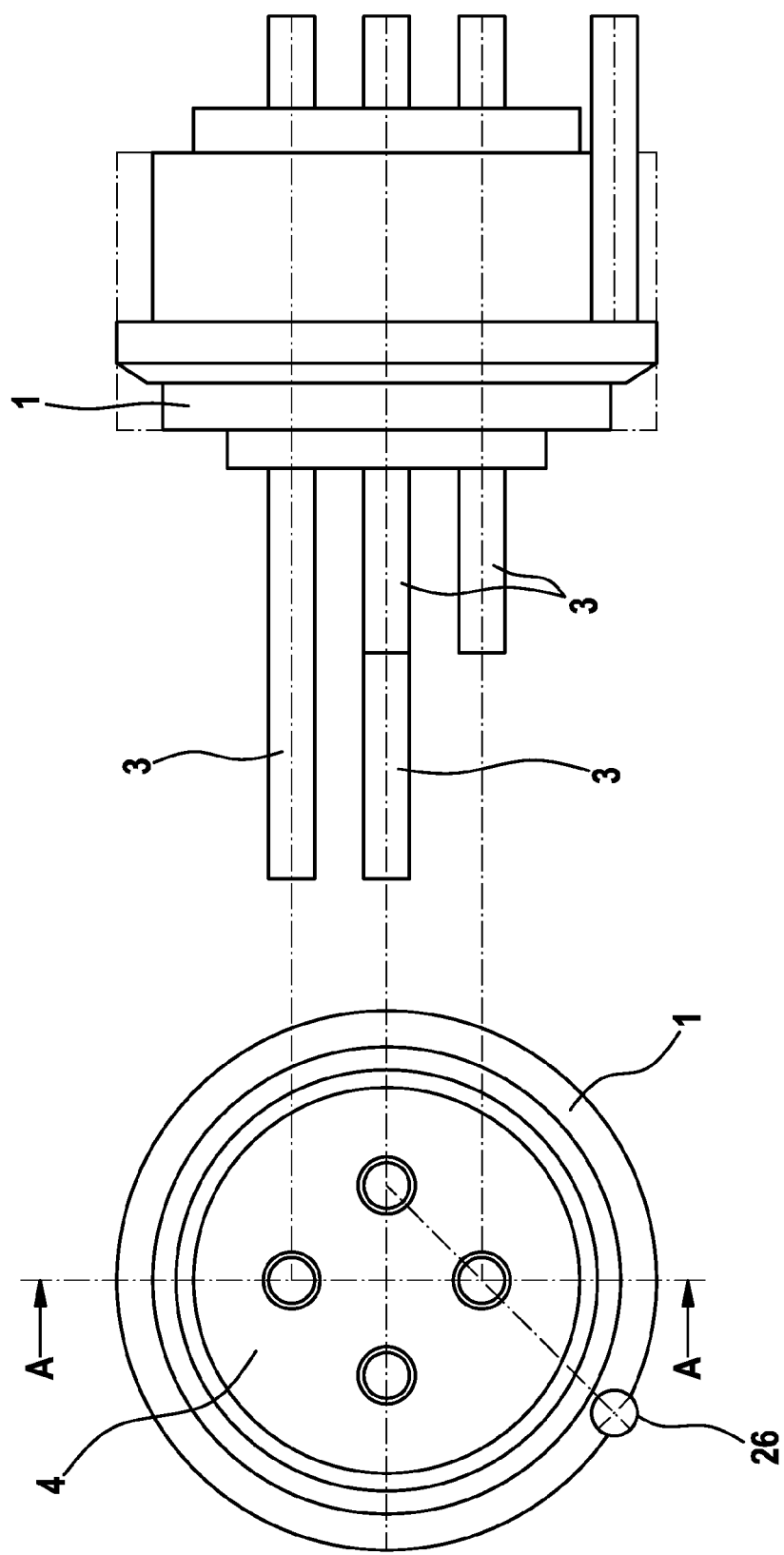

ELECTRICAL FEEDTHROUGH

This application takes priority from German Patent Application DE 10 2006 041 940.5 filed 7 Sep. 2006, the specification of which is hereby incorporated herein by reference

BACKGROUND OF THE INVENTION

1. Field of the Invention

The present invention relates to an electrical feedthrough to be inserted into an opening of an implantable electrical treatment device. Such electrical treatment devices are, for example, implantable cardiac pacemakers, implantable cardioverters/defibrillators, or cochlear implants

2. Description of the Related Art

The electrical feedthrough has an electrically insulating insulation body, through which at least one electrically conductive terminal pin passes, which is connected to the insulation body hermetically sealed using a solder.

Electrical feedthroughs of this type are used for the purpose of producing an electrical connection between a hermetically sealed interior of a treatment device and the exterior of the treatment device. In known electrotherapy devices, such as cardiac pacemakers or cardioverters/defibrillators, a hermetically sealed metal housing is typically provided, which has a terminal body, also called a header, on one side, which carries terminal sockets for connecting electrode lines. The terminal sockets have electrical contacts which are used for the purpose of electrically connecting electrode lines to the control electronics in the interior of the housing of the cardiac pacemaker. A feedthrough, which is inserted hermetically sealed into a corresponding housing opening, is typically provided where the electrical connection enters the housing of the cardiac pacemaker.

Electrical feedthroughs of this type are frequently implemented as filter feedthroughs. In this case, the apparatuses carry an electrical filter, which is used for the purpose of short-circuiting external high-frequency electric interference, so that corresponding signals are fed, if at all, only strongly damped to the control electronics in the interior of the housing and the control electronics first experience interference at significantly greater signal strengths of the electrical interference than would be the case without the electrical filter. A filter of this type is typically formed by a filter body which is connected like a capacitor between a device ground and a particular electrical line passing through the feedthrough.

Such an electrical line passing through the feedthrough is typically formed by an electrically conductive terminal pin, which passes through a through opening in an electrically insulating insulation body. The electrically conductive terminal pin projects on both sides beyond the particular face of the insulation body, so that on both sides of the insulation body—and thus on both sides of the electrical feedthrough—continuing electrical lines may be connected to the terminal pin in each case—by soldering or welding, for example. A possible gap between a through opening in the insulation body, through which a particular terminal pin passes, and the terminal pin itself, is typically closed hermetically sealed using a solder, normally gold solder.

Manifold electrical feedthroughs of this type are known from the prior art. Examples may be found in U.S. Pat. No. 6,934,582, U.S. Pat. No. 6,822,845, U.S. Pat. No. 6,765,780, U.S. Pat. No. 6,643,903, U.S. Pat. No. 6,567,259, U.S. Pat. No. 6,768,629, U.S. Pat. No. 6,765,779, U.S. Pat. No. 6,566,978, and U.S. Pat. No. 6,529,103.

In spite of the manifold known feedthroughs, there is still the demand for improving them in regard to producibility and properties.

BRIEF DESCRIPTION OF THE INVENTION

This object is achieved according to the present invention in that glass or glass ceramic is provided as the material of the solder between insulation body and terminal pin. In particular if ceramic insulation bodies are used, a reduction of the production costs and an improvement of the reliability result simultaneously in that a solder may be connected directly to both the insulation body and also to the terminal pin and possibly the flange, without complex preparation work being necessary for this purpose, for example, in the ceramic production or a coating of the insulation body.

This provides the advantage that the number of components and process steps during production is reduced.

A further important advantage is that the glass or glass-ceramic solder material is electrically insulating and may thus be connected simultaneously to the flange and the pin. In contrast, with a conductive solder such as gold, pin and flange require at least two separate solder reservoirs, because otherwise an electrical short-circuit would occur between pin and flange. Therefore, an electrically insulating solder such as glass or glass ceramic allows simpler and more compact constructions of electrical feedthroughs.

A biocompatible surface of the insulation body on its exterior (in regard to the installed state) may also be achieved in this way without further measures.

The latter advantage is particularly provided if the insulation body comprises a ceramic material, which preferably contains $Al_2O_3$.

The degree of biocompatibility is also increased if the glass or glass-ceramic solder material is implemented as biocompatible and/or the ceramic insulation body and/or the flange are molded in such a way that a potential access of bodily fluid to the solder is additionally made more difficult via one or more tightly guided edges.

The soldering course of the glass or the glass ceramic becomes more controllable if, in addition to the insulation body facing toward the body, a further insulation body is also soldered onto the other side of the glass or glass-ceramic solder, so that the glass or glass-ceramic solder is enclosed in the flange hole from both sides by insulation bodies and both insulation bodies are soldered together with the flange and the pin.

The feedthrough is especially suitable for high voltage applications, such as defibrillators, if the insulation ceramic is shaped in such a way that long insulation distances arise on the surface and in the volume. Suitable shapes are, for example, bulges and edges. Such shapes are preferably implemented on the side of the feedthrough facing toward the body.

Accordingly, it is a separate idea, to be implemented independently of the other features of a feedthrough described here, to mold the insulation body in such a way that it offers long insulation distances on the surface and in the volume, i.e., for example, has a surface having corresponding depressions or protrusions which are used to lengthen the insulation distances.

Moreover, shapes of this type offer stable anchoring possibilities for the header, so that its attachment to the housing of the implant becomes more secure.

The terminal pin preferably comprises metal, which preferably contains platinum and is especially preferably a platinum-iridium alloy. Niobium, tantalum, and titanium, and their suitable alloys come into consideration as further, especially biocompatible and corrosion-resistant metals for the pin. Terminal pins of this type have the desired biocompatibility, are corrosion-resistant, and may be processed reliably.

In a preferred embodiment variation, the terminal pin or the terminal pins are each inserted into a through hole in the insulation body and connected mechanically solidly and hermetically sealed thereto by the solder formed by glass and/or glass ceramic. The flange either has a separate through hole for each pin or multiple pins share a joint through hole.

In a further embodiment variation, each pin has its separate insulation body, with the advantage that the insulation bodies may be implemented rotationally symmetric, e.g., cylindrical, and are simply producible.

To improve the soldered connection between terminal pin and insulation body, a corresponding through opening for the terminal pin may have an expansion on at least one longitudinal end, so that a space arises between terminal pin and expanded through opening, which is filled with glass or glass-ceramic solder. The space described may preferably be implemented as an annular space and is referred to for the sake of simplicity as a cavity in the following; it is expressly noted that the cavity may also assume any other shape. For example, the spaces may overlap and form a shared space which is filled with glass or glass-ceramic solder.

To be suitable for treatment devices whose electrical components in the interior of the housing are to be connected via multiple electrical lines, for example, to one or more electrode lines, the feedthrough is preferably implemented as multipolar and has multiple terminal pins, preferably running parallel to one another, and a corresponding number of through holes. These through holes preferably each only have a diameter on one longitudinal end which is significantly greater than the external diameter of the terminal pin, so that a cavity arises between terminal pin and hole. These cavities are preferably all situated on the same front face of the insulation body.

The attachment of electrical lines of a header is made easier if the terminal pins have different lengths on the exterior of the feedthrough (in relation to the installed state). The attachment of the electrical lines is also made easier in many cases if the pins are flattened, bent, or brought into the shape of nail heads or other suitable shapes on their ends.

To achieve the greatest possible distance of the terminal pins from one another in an insulation body which is as small as possible, the terminal pins are situated uniformly distributed on a circular arc concentric to the insulation body, preferably running parallel to one another. Alternatively, however, the terminal pins may also be situated linearly in one plane in the insulation body. This may make further manufacturing steps in the pacemaker production easier. A linear configuration in which two or more rows of terminal pins are each situated offset to one another in the insulation body also comes into consideration.

In particular in the first of the three last-mentioned embodiment variants, it is advantageous if the circular body has a cross-sectional area running transversely to the longitudinal direction of the terminal pin or terminal pins, which is round and preferably circular.

The insulation body is preferably enclosed transversely to the longitudinal direction of the pins by a sleeve-like metallic flange. The flange preferably comprises a material which is identical in its composition to the metallic housing of the treatment device as much as possible. The flange is either worked out of a solid material by turning or milling, for example, or produced by a suitable sintering process. In the latter case, the flange body may be penetrated by small pores, which do not impair the hermetic seal of the flange, however.

A flange of this type may, for example, be connected hermetically sealed to a metallic housing of the treatment device by welding. Flange and insulation body are connected hermetically sealed to one another.

The feedthrough is preferably implemented as a filter feedthrough having a filter body. The filter body has disk-shaped capacitor electrodes running parallel to one another, which are alternately electrically connected to the flange and to a terminal pin.

In connection with the latter embodiment variant, the flange preferably extends far enough beyond the inner face of the insulation body that the flange also encloses the filter body over at least the majority of its length and in this way is easy to connect electrically to the capacitor electrodes of the filter body.

If the pins comprise iridium, niobium, tantalum, titanium, or similar materials which may not be soft-soldered directly, the electrically conductive connection of the pins to the capacitor electrodes of the filter body via electrically conductive adhesive or by soft soldering is made significantly easier if the pins are gilded using gold solder. The gilding may be restricted to the areas of the pins which are decisive for the electrical connection of the pins to the capacitor electrodes of the filter body.

In an idea which is independent of the present invention and is protectable separately, the capacitor electrodes of the filter body are soldered to the pins and the flange directly using gold solder, for example. A particularly heat-resistant filter body is required for this purpose. A filter feedthrough may be manufactured cost-effectively in a single soldering step in this way. In this case, the application of further, sealing gold or glass-ceramic solder may be dispensed with, instead, the insulation body is coated with iridium, niobium, titanium, tantalum, or their suitable alloys at suitable points, for example.

To judge the hermetic seal of the implant interior to the environment formed by the feedthrough, it is advantageous if the areas of the sintered connections or soldered connections (using glass, glass-ceramic, or gold solder) are accessible for a helium leak test and are not concealed by a filter body and its electrically conductive connections to the pins and the flange.

The ability to test the hermetic seal of the feedthrough may be ensured in multiple ways:

A through opening in the electrical filter body.

A through opening in one of the electrically conductive connections between the filter body and the pins and/or the flange.

The filter body is integrated in a socket which is connected via spot welds to the flange; the helium gas passage is ensured between the spot welds.

The electrical connection of the filter to the flange or to the pins is produced by a (spring) terminal, either the flange being shaped in such a way that the springs are a component of the flange, or a separate spring body producing the electrical connection between the flange and the filter. The desired helium gas passage occurs in this case between the terminal points.

In one variant, the capacitor electrodes of the filter are already integrated in the insulation body, so that a separate filter body is dispensed with. A possible embodiment is that the same ceramic insulation material ($Al_2O_3$) is used as the dielectric material between the capacitor electrodes as on the surface. In a further embodiment variant, a material adapted for the electrical filter function (e.g., $BaTiO_3$ or a similar ceramic material of high permittivity) is located between the capacitor electrodes, while a biocompatible insulating material is located on the surface (e.g., $Al_2O_3$).

Finally, to ensure good mounting ability and a good seal between flange and insulation body, the insulation body preferably has a peripheral shoulder in the exterior peripheral surface, which works together with a corresponding shoulder in the inner wall of the flange when the two shoulders on the peripheral surface of the insulation body and in the inner wall of the flange run diagonally in relation to the longitudinal direction of the feedthrough, so that conical surfaces working together with one another result, and the shoulder also makes centering the insulation body in relation to the flange easier.

BRIEF DESCRIPTION OF THE DRAWINGS

The present invention will now be explained in greater detail on the basis of exemplary embodiments with reference to the drawings. In the figures:

FIGS. 4a and 4b: show a front view (FIG. 4a) and a side view (FIG. 4b) of a multipolar filter feedthrough according to the present invention;

DETAILED DESCRIPTION OF THE INVENTION

Figure 1:
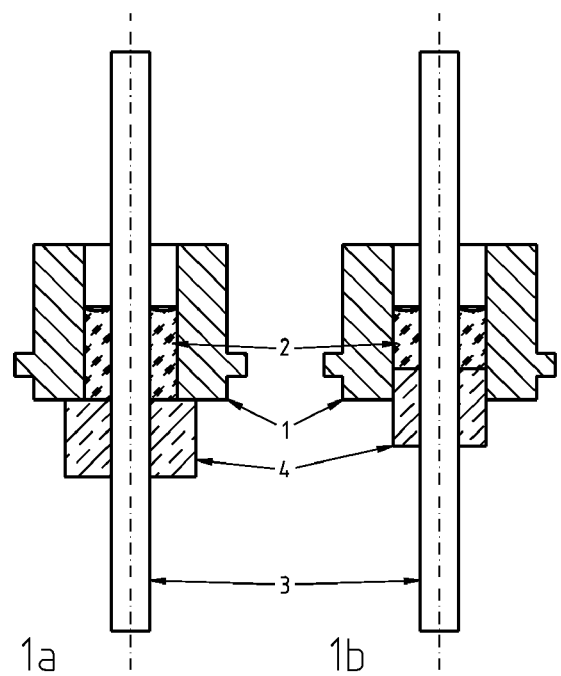
FIGS. 1a through 1h: show various embodiment variations of a unipolar feedthrough without a filter body longitudinal section, and/or a linear, multipolar feedthrough in cross-section.
FIGS. 1i through 1o: show different unipolar feedthroughs as filter feedthroughs in longitudinal section, and/or various linear, multipolar filter feedthroughs in cross-section.
FIG. 1p: shows a filtered, unipolar feedthrough having two variants of the gas access to check the hermetic seal in a top view.
Figure 1:
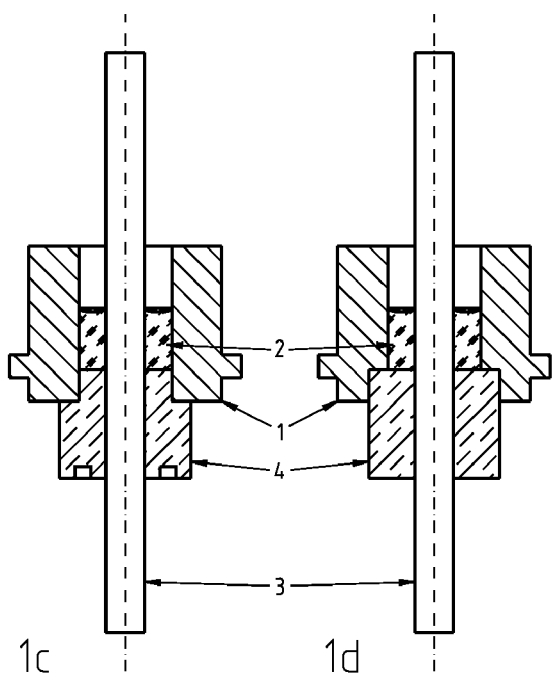
Figure 1:
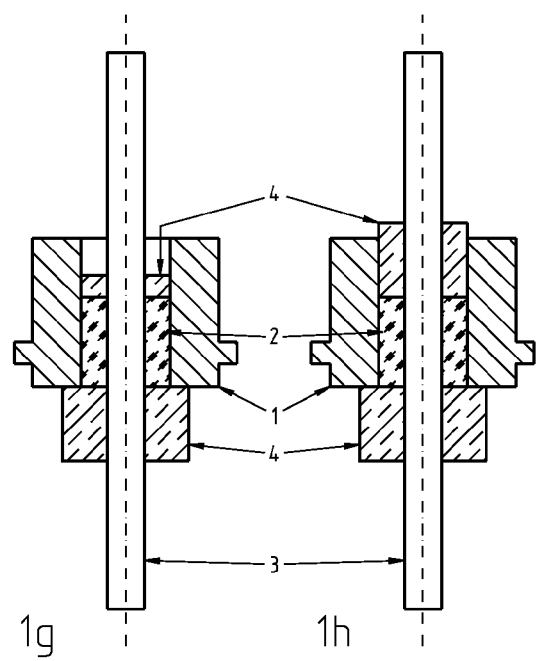
Figure 1:
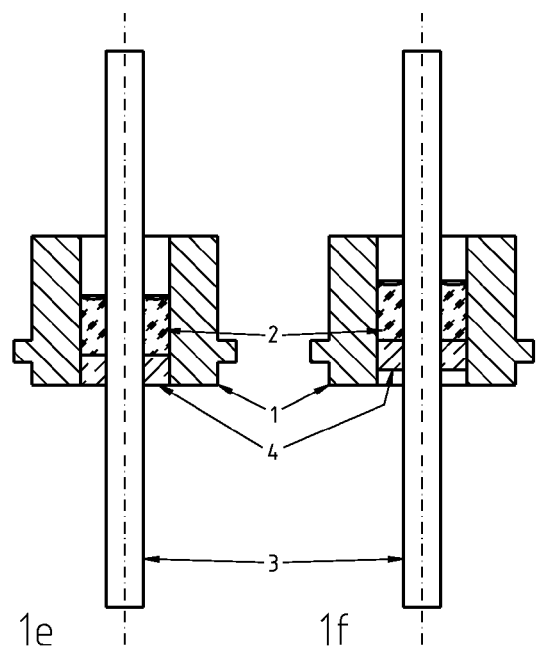
Figure 1:
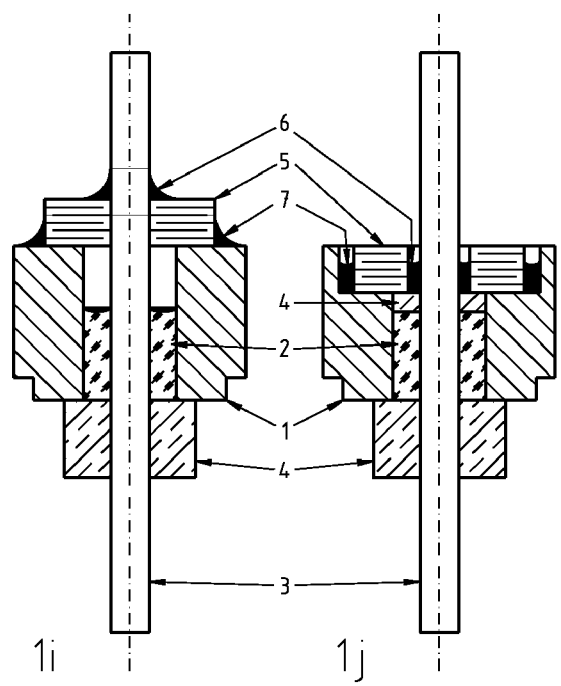
Figure 1:
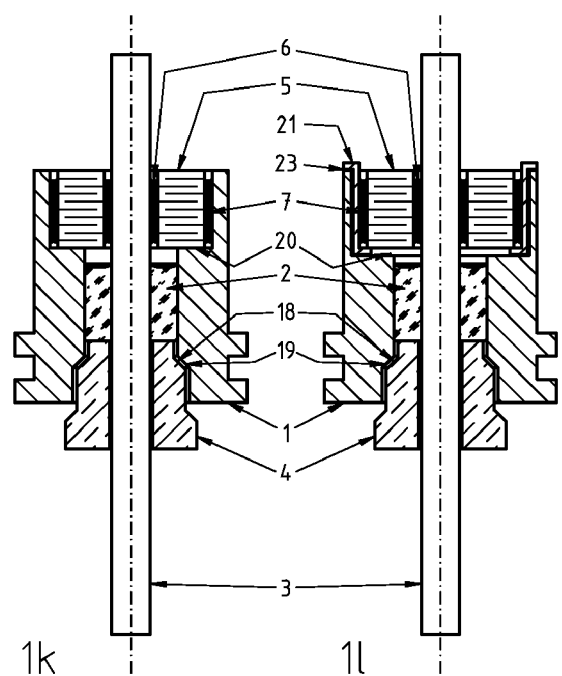
Figure 1:
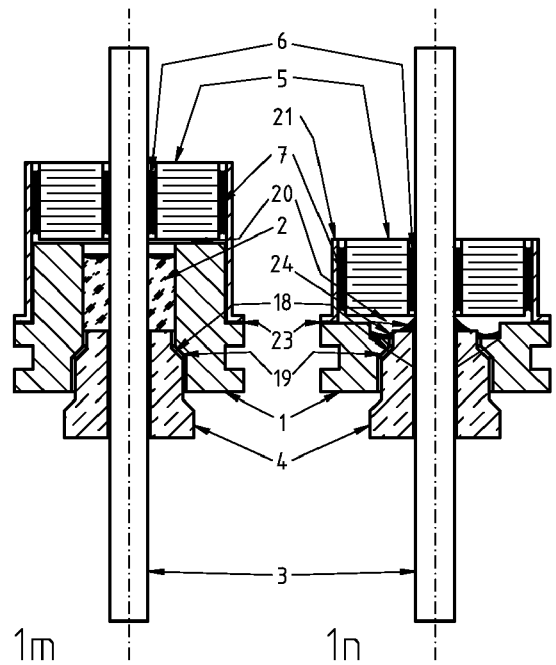
Figure 1:
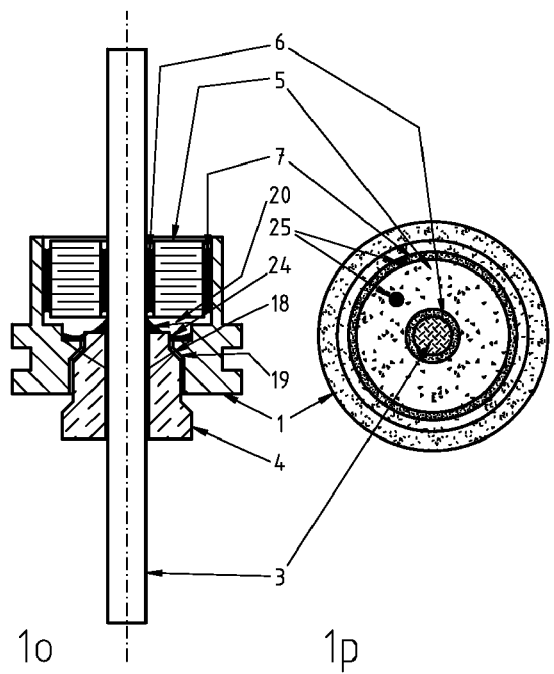
Figure 2:
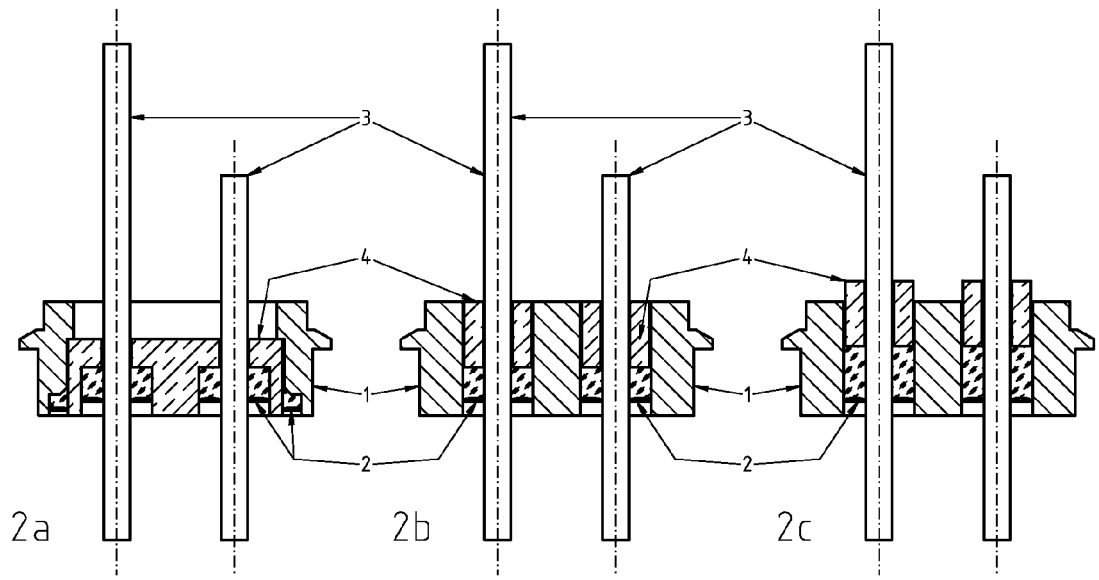
FIGS. 2a through 2i: show various variants of multipolar feedthroughs in longitudinal section.
FIGS. 2j through 2o: show various variants of multipolar feedthroughs as filter feedthroughs in longitudinal section.
Figure 2:
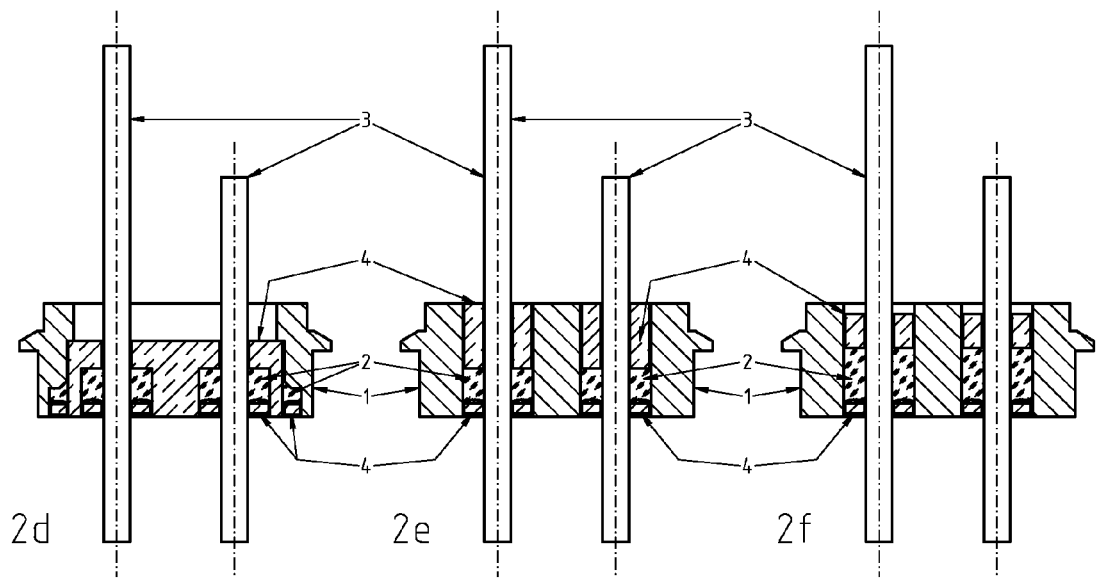
Figure 2:
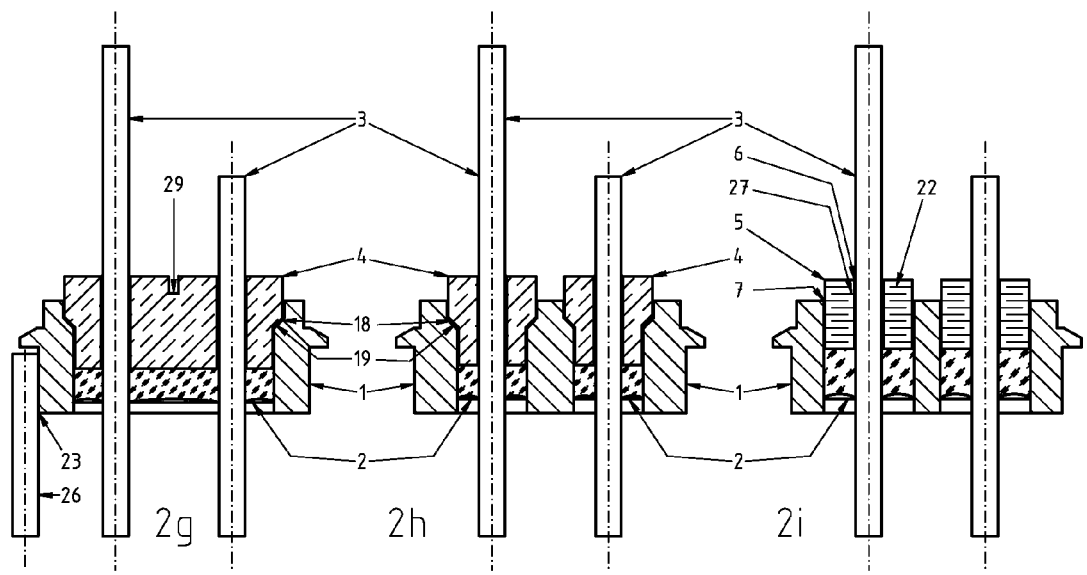
Figure 2:
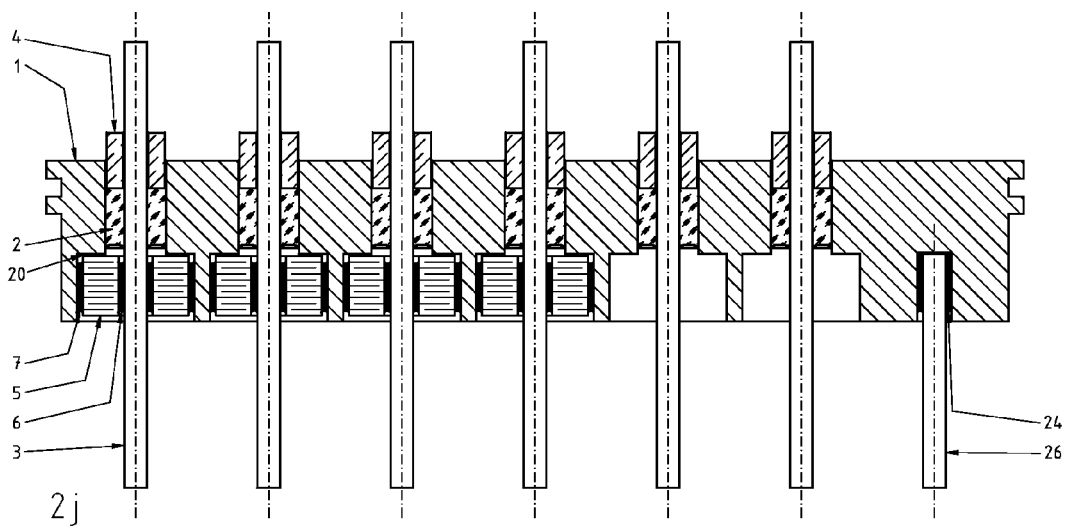
Figure 2:
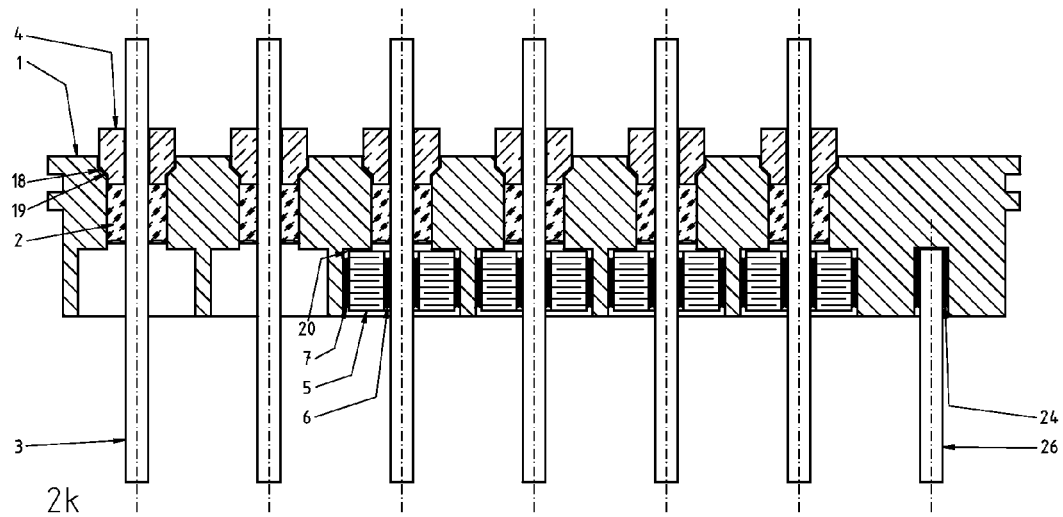
Figure 2:
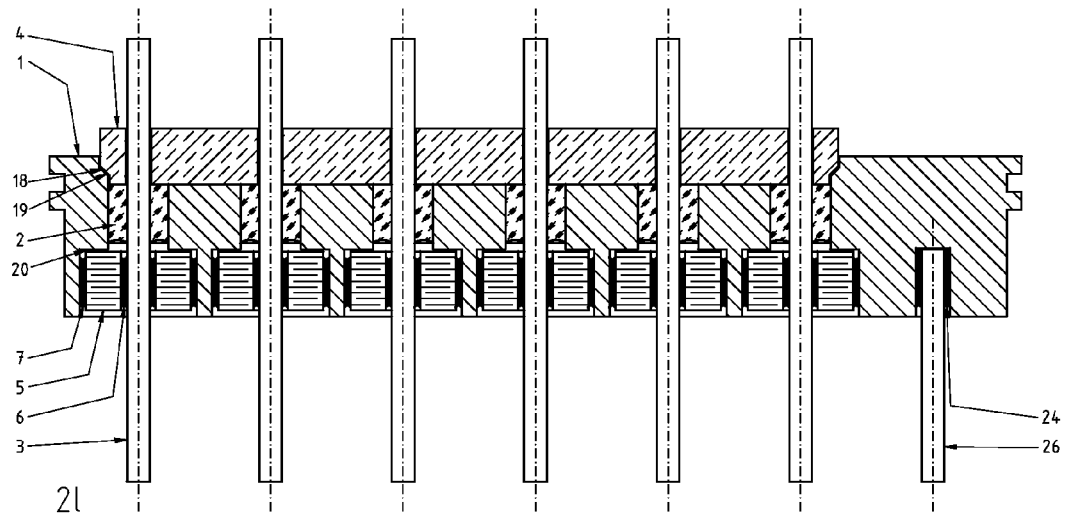
Figure 2:
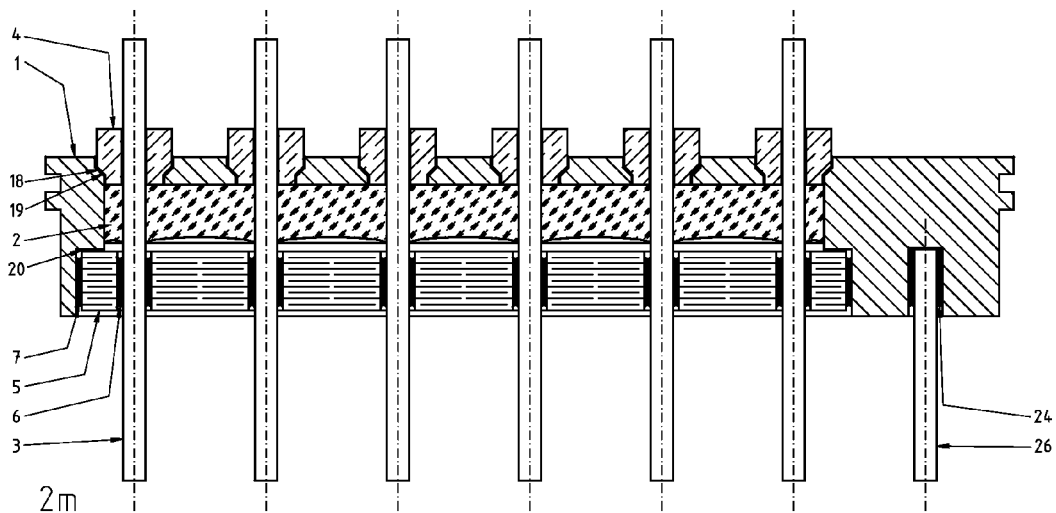
Figure 2:
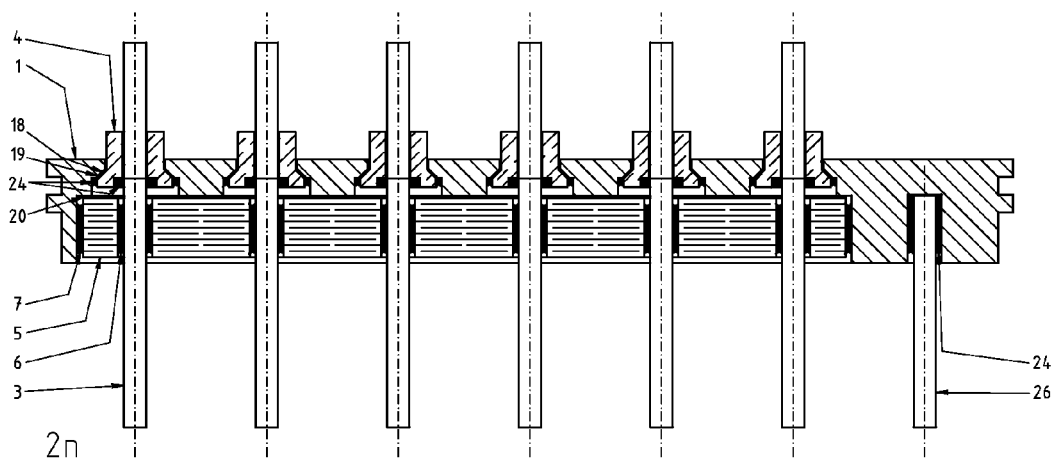
Figure 2:
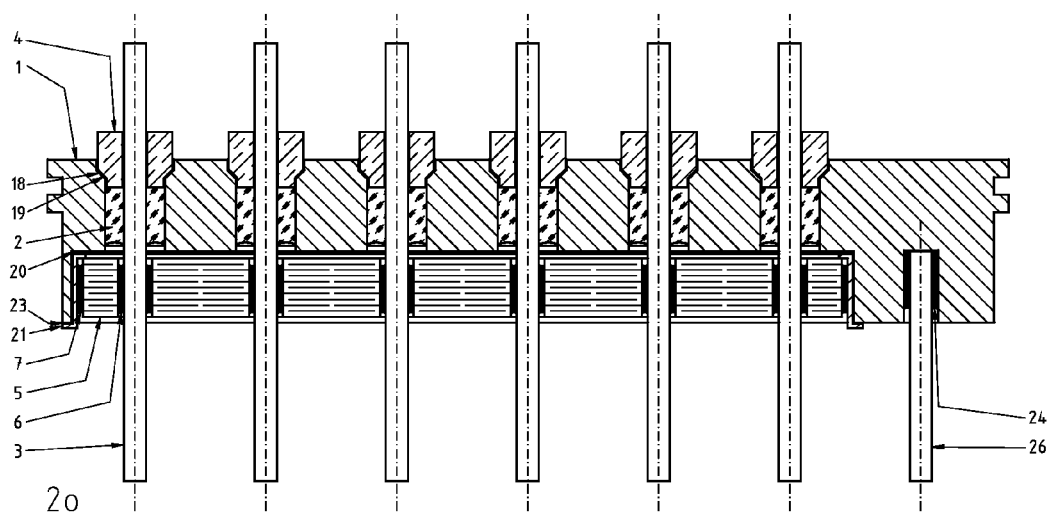

All of the feedthroughs illustrated in the exemplary embodiments according to FIGS. 1a through 4c have a flange 1 and at least one terminal pin 3. The terminal pin 3 is electrically insulated in relation to the flange 1 with the aid of at least one insulation body 4 made of ceramic and with the aid of glass and/or glass-ceramic solder 2, which connects the pin 3 to the insulation body 4 and to the flange 1.

The structure of the particular feedthrough shown results from the following nomenclature:

The flange is identified in all embodiment variations by reference numeral 1.

The glass and/or glass-ceramic solder is identified in all embodiment variations by reference numeral 2.

The terminal pins are identified in all embodiment variations by reference numeral 3.

Insulation bodies made of ceramic, in particular made of $Al_2O_3$, are identified in all embodiment variations by reference numeral 4.

In the embodiment variations which show a filter feedthrough, the particular filter body is identified by reference numeral 5. In these embodiment variations (FIGS. 1i-1p and 2j-2o) the reference numerals 6 and 7 identify an electrically conductive connecting material, such as an electrically conductive thermoplastic or an electrically conductive (metal) solder.

FIG. 1a shows a hybrid glass/ceramic feedthrough which is unipolar and/or linearly multipolar in cross-section. The glass and/or glass-ceramic solder 2 simultaneously hermetically connects the pin or the pins 3 to the flange 1 and to the (ceramic) insulation body 4. In the unipolar case, the insulation body 4 has a simple, cylindrical shape. The insulation body 4 is seated on the front face of the flange 1. The advantage results that the glass and/or glass ceramic 2 is prevented from flowing out downward during the soldering, the surface of the insulation body 4 is biocompatible on the exterior (in the figure: on top), no coating of the insulation body 4 is necessary, visual checking of the component from the interior is possible (in the figure: from top to bottom), the insulation body 4 is to be produced simply and cost-effectively, and a good mechanical hold for the header on the projecting insulation body 4 is provided.

The embodiment variation according to FIG. 1b is similar to that from FIG. 1a, but the insulation body 4 projects into the hole of the flange 1. In this way, automatic centering of the pin 3 in relation to the hole of the flange and a smaller insulation body 4 having smaller possible pitch dimension (distance from pin to pin) result as additional advantages.

The embodiment variation according to FIG. 1c is similar to that from FIG. 1b, but the insulation body 4 is implemented as a double cylinder: one cylinder projects into the hole of the flange 1, the other abuts the front face of the flange 1 externally. In addition, the insulation body 4 has a slot (depression) on the front face of the large cylinder as a variant, which extends the insulation distances and increases the high-voltage resistance. An additional edge between the flange 1 and the insulation body 4 to reduce the interaction between the external area and the glass surface (keyword: dendritic growth) as well as automatic centering of the insulation body 4 and the pin 2 in the hole of the flange 1 result as advantages. The insulation body is molded in a more complicated way for this purpose.

The embodiment variation according to FIG. 1d is similar to FIG. 1a, but the insulation body 4 projects into a shoulder in the flange 1. Automatic centering of the insulation body 4 and the pin 2 in the hole of the flange 1, a geometrically simpler and more cost-effective insulation body 4, as well as an additional edge between the flange 1 and the insulation body 4 to reduce the interaction between the external area and the glass surface (keyword: dendritic growth) result as advantages.

The embodiment variation according to FIG. 1d is similar to FIG. 1b, but the insulation body 4 terminates flush with the front face of the flange 1. A more compact construction results as an advantage.

The embodiment variation according to FIG. 1f is similar to that from FIG. 1e, but the front face of the insulation body 4 is inside the hole of the flange 1. The advantage results from this that the header is mechanically geared in the pocket hole up to the insulation body 4.

The embodiment variation according to FIG. 1g is similar to that from FIG. 1a, but the glass solder 2 in the flange hole is delimited on top (interior of the implant) by a further insulation body 4. A limitation of the solder volume to a defined area, improved control of the soldering process (no flowing away of the glass or glass-ceramic solder 2), and thus higher yields in the manufacturing process, centering of the pin 2 in relation to the hole of the flange 1 at two points instead of one, so that required geometries are maintained more securely, result as advantages here. However, a higher equipment outlay due to a further component also results.

The embodiment variation according to FIG. 1h is similar to that from FIG. 1g, but the second insulation body 4 projects out of the hole of the flange 1. This makes it easier to handle the second insulation body 4 because of its size.

The embodiment variation according to FIG. 1i is similar to that from FIG. 1a, but having an attached filter body 5 via an electrically conductive point 6 on the pin 3 and an electrically conductive point 7 on the flange 1. The points 6 and 7 do not have to be produced from the same material. Optional through openings 25 through the filter body 5 and/or the solder points 6 and/or 7 for checking the hermetic seal are not shown. A filter feedthrough having greater freedom in the variability of the filter size advantageously results in this way.

The embodiment variation according to FIG. 1j is similar to that from FIG. 1i, but the filter body 5 is located in a cavity of the flange 1 and the pin 3 is fixed by two insulation bodies 4 and the glass and/or glass-ceramic solder 2 is delimited in its course. A more compact construction thus results.

The embodiment variation according to FIG. 1k is similar to that from FIG. 1j, but the insulation body 4 and the flange 1 have bevels 18 and 19 which are tailored to one another and cause especially good centering of the insulation body 4 in relation to the flange 1. In addition, the insulation body 4 is shaped in its further course outside the flange 1 in such a way that it is designed for higher operating voltages, as occur in defibrillators, for example, because it insures longer current paths between the flange 1 and the pin 3. In addition, the special shaping of the insulation body 4 causes improved retention of the header. A free space 20 between the filter body 7 and the flange 1, which allows a gas access to the glass and/or glass-ceramic soldered point to check the hermetic seal, is also indicated.

The embodiment variation according to FIG. 1l is similar to that from FIG. 1k, but the filter body 5 is soldered into a socket 21, which is in turn connected via soldered points 23 to the flange 1. In this way, a gas access between the soldered points 23 is ensured for checking the hermetic seal.

The embodiment variation according to FIG. 1m is similar to that from FIG. 1l, but the socket 21 comprises the flange 1.

The embodiment variation according to FIG. 1n is similar to that from FIG. 1m, but does not represent an embodiment variation of the claimed invention, because instead of an electrically insulating glass and/or glass-ceramic solder 2, a metallic solder 24 is provided for connecting the insulation body 4 to the pin 3 and the flange 1. For this purpose, a suitable metallic coating of the insulation body 4 is required on at least two different points which do not overlap, so that the metallic solder 24 may produce a solidly adhering, hermetically sealed connection to the insulation body 4.

The embodiment variation according to FIG. 1o is similar to that from FIG. 1n, but the filter body 5 is connected directly in a cavity of the flange 1 to the flange 1 via the electrically conductive connection 7 and to the pin 3 via the electrically conductive connection 6.

FIG. 1p shows the same feedthrough as in FIG. 1o, but in a top view of the filter body 5. Through openings 25 for checking the hermetic seal in the filter body 5 and/or in the electrically conductive connection 7 are indicated.

It results as a shared feature from the embodiment variations 1a through 2o that the particular glass solder 2 fills up a cavity which is defined by at least one particular insulation body 4 made of ceramic as well as at least one terminal pin 3 and possibly additionally by a flange 1.

In addition, it is to be noted that the feedthroughs as shown in FIG. 1 are all unipolar feedthroughs. In addition, the cross-sections according to FIGS. 1a-1o may also be understood as cross-sections through linear, multipolar feedthroughs, which are more or less produced by arraying a series of unipolar feedthroughs.

FIGS. 1j through 1p show for exemplary purposes that the feedthroughs shown may also be implemented as filter feedthroughs. It is to be noted that the filter feedthrough according to FIG. 1i, except for the filter body 5 and the electrically conductive connections 6 and 7, corresponds to the feedthrough from FIG. 1a.

FIG. 2a shows an unfiltered, hybrid glass/ceramic feedthrough which is bipolar or multipolar and/or double linearly multipolar in cross-section. The glass and/or glass-ceramic solder 2 connects the pins 3 and the flange 1 hermetically to the (ceramic) insulation body 4. The insulation body 4 may have a simple, cylindrical shape, but may also be oval or elongate. The insulation body 4 is located in a cavity of the flange 1 and is seated on a shoulder in the flange. All pins 3 are located in a shared insulation body 4, but at least two pins 3 are located in each insulation body 4. The pins 3 may—as indicated here—be implemented having different lengths. The top side of the feedthrough is located in the external area of the implant in this image. During the soldering in the production of the feedthrough, the orientation is reversed, so that the glass and/or glass-ceramic solder 2 rests on the flange 1 and the insulation body 4, for example. An advantage is that the glass and/or glass-ceramic solder 2 is prevented from flowing out upward during the soldering. In addition, the insulation body 4 has a biocompatible surface on its exterior side (in the figure: top). Coating the insulation body 4 is not necessary. Moreover, it is possible to check the component visually from the interior (in the figure: direction downward).

The feedthrough illustrated in FIG. 2b is similar to that illustrated in FIG. 2a, but at least two pins 3 each have a separate insulation body 4 in separate holes of the flange 1. The insulation body 4 terminates flush with a front face of the flange 1. Higher mechanical stability due to the cell-like structure of the (metallic) flange 1 results as an advantage from this. In addition, the insulation body 4 may be shaped cylindrically in a mechanically simple way and therefore universally and cost-effectively.

The feedthrough illustrated in FIG. 2c is similar to that illustrated in FIG. 2b, but the insulation body 4 extends beyond the front face of the flange 1. A larger insulation distance and an improved mechanical hold for the header of the implant result as advantages.

The feedthrough illustrated in FIG. 2d is similar to that illustrated in FIG. 2a, but the glass and/or glass-ceramic solder 2 is delimited by further insulation bodies 4 on both sides. Improved control of the solder course and centering of the pin 3 at two points results from this.

The feedthrough illustrated in FIG. 2e is similar to that illustrated in FIG. 2b, but the glass and/or glass-ceramic solders 2 are delimited by further insulation bodies 4 on both sides. Improved control of the solder course and centering of the pin 3 at two points also results here.

The feedthrough illustrated in FIG. 2f is similar to that illustrated in FIG. 2e, but at least two outwardly (upwardly in the drawing) directed insulation bodies 4 are countersunk in the holes of the flange 1.

The feedthrough illustrated in FIG. 2g is similar to that illustrated in FIG. 2a, but the insulation body 4 projects out of the hole of the flange 1. In addition, the insulation body 4 has a bevel 19, which corresponds to a bevel 18 of the flange 1 and causes especially good centering of the insulation body 4 in relation to the flange 1. Moreover, the insulation body 4 has a so-called "slot" 29, which extends the insulation distance between the pins 3 and offers a better hold for the header of the implant. A shared glass and/or glass-ceramic solder 2 connects at least two pins 3 hermetically sealed to the flange 1 and the insulation body 4. Optionally, a ground pin 26 is attached to the flange 1 via a connection 23. The connection 23 is preferably implemented by welding.

The feedthrough illustrated in FIG. 2h is similar to that illustrated in FIG. 2c, but the insulation body 4 and the flange 1 have bevels 19 and 18 corresponding to one another, which cause the centering of the insulation body 4 in relation to the flange.

The feedthrough illustrated in FIG. 2i is similar to that illustrated in FIG. 2c, but insulation bodies 4 are replaced by filter bodies 5. The filter bodies 5 have electrode plates 22 and 27, which are alternately in contact with the pin 3 via electrically conductive connections 6 and with the flange 1 via electrically conductive connections 7. The electrically conductive connections 6 and 7 may comprise the same material. A glass and/or glass-ceramic solder 2 ensures the hermetically sealed connection of the filter body 5 to the pin 3 and the flange 1. The dielectric material of the filter body 5 preferably comprises a biocompatible, preferably ceramic material or the filter body 5 is provided with a biocompatible coating.

FIG. 2j shows a filter, hybrid glass/ceramic feedthrough, preferably linearly multipolar and/or double or multiple linearly multipolar in cross-section. The glass and/or glass-ceramic solder 2 connects the pins 3 and the flange 1 hermetically sealed to the preferably ceramic insulation body 4. The insulation body 4 preferably has a simple, cylindrical shape, but may also be oval or elongate perpendicular to the cross-sectional view shown. The insulation bodies 4 are located in holes of the flange 1. All pins 3 each have a separate insulation body 4, but two or more pins 3 may also be located in each insulation body 4 perpendicularly to the cross-sectional view. The pins 3 may—as not indicated here—be implemented having different lengths and/or be shaped suitably for better attachment on their ends, e.g., flattened, nail-shaped, bent, etc. In this image, the upper side of the feedthrough is located in the exterior area of the implant. During the soldering while the feedthrough is produced, the orientation is reversed, so that the glass and/or glass-ceramic solder 2 rests on the insulation body 4, for example. In this image, electrical filter bodies 5 are attached to some of the pins 3, if necessary also to all pins 3 or—in an unfiltered version—to none of the pins 3. The electrically conductive connection of the filter bodies 5 to the pins 3 is produced here via a metallic solder and/or an electrically conductive compound 6. The electrically conductive connection of the filter body 5 to the flange 1 is also executed via the material 7, the materials 6 and 7 being able to comprise the same substance. Through openings 25 which lead through the connections 6 or 7, through the filter bodies 5, or through the walls of the flange 1 to free spaces 20 are not shown, so that the hermetic seal of the finished component may be checked. Alternatively, the electrically conductive connections 6 and/or 7 may be implemented by terminals or by spring force, so that the through openings 25 described may be dispensed with. Optionally, a ground pin 26 is connected to the flange 1 via an electrically conductive material 24, preferably a metallic solder. The advantage also results here that the glass and/or glass-ceramic solder 2 is prevented from flowing out upward during the soldering. A further advantage is a biocompatible surface of the insulation body 4 on its exterior side (in the figure: direction upward). No coating of the insulation body 4 is necessary. In addition, a visual check of the component from the inside (in the figure: direction downward) before the attachment of the filter bodies 5 is possible. A relatively small pitch dimension (distance from pin to pin) is possible due to the shared flange 1 and especially mechanically stable together with separate holes.

The embodiment variation according to FIG. 2k largely corresponds to that from FIG. 2j, but the insulation bodies 4 have bevels 19, which correspond to bevel 18 of the flange 1, so that the insulation body 4 obtains improved centering in the holes of the flange 1. The filter body 5 filters signals to other pins 3 in relation to FIG. 2j.

The embodiment variation according to FIG. 2l largely corresponds to that from FIG. 2k, but the pins 3 are guided through a shared insulation body 4. All pins 3 are provided with separate filter bodies in this embodiment variation.

The embodiment variation according to FIG. 2m largely corresponds to that from FIG. 2k, but the insulation bodies 4 and the pins 3 are connected hermetically sealed to the flange 1 via a shared glass and/or glass-ceramic solder 2. A shared filter body 5 is also used for the pins 3 in this embodiment.

The embodiment variation according to FIG. 2n does not show an embodiment variation of the present invention, because according to the embodiment variation from FIG. 2n—which is otherwise similar to that from FIG. 2m—the insulation body 4 is connected hermetically sealed to the pins 3 and the flange 1 with the aid of a preferably metallic solder 24, so that the glass and/or glass-ceramic solder 2 may be dispensed with. The insulation body 4 must have a suitable coating for this purpose, so that it may be wetted with the solder 24.

The embodiment variation according to FIG. 2o is similar to that from FIG. 2k, but the pins 3 are filtered via a shared filter body 5, which is electrically connected to a socket 21 via a material 7. The socket 21 is electrically and mechanically connected solidly to the flange 1 at suitable points 23, preferably by welded bonds. A gas access into the free space 20 between the glass and/or glass-ceramic solder 2 and the filter body 5 and/or the feedthrough 21 is possible between the points 23, so that additional through openings 25 on the filter body 5 or the connections 6 and 7 may be dispensed with and it is possible to check the hermetic seal on the component in the finished state.

Figure 3:
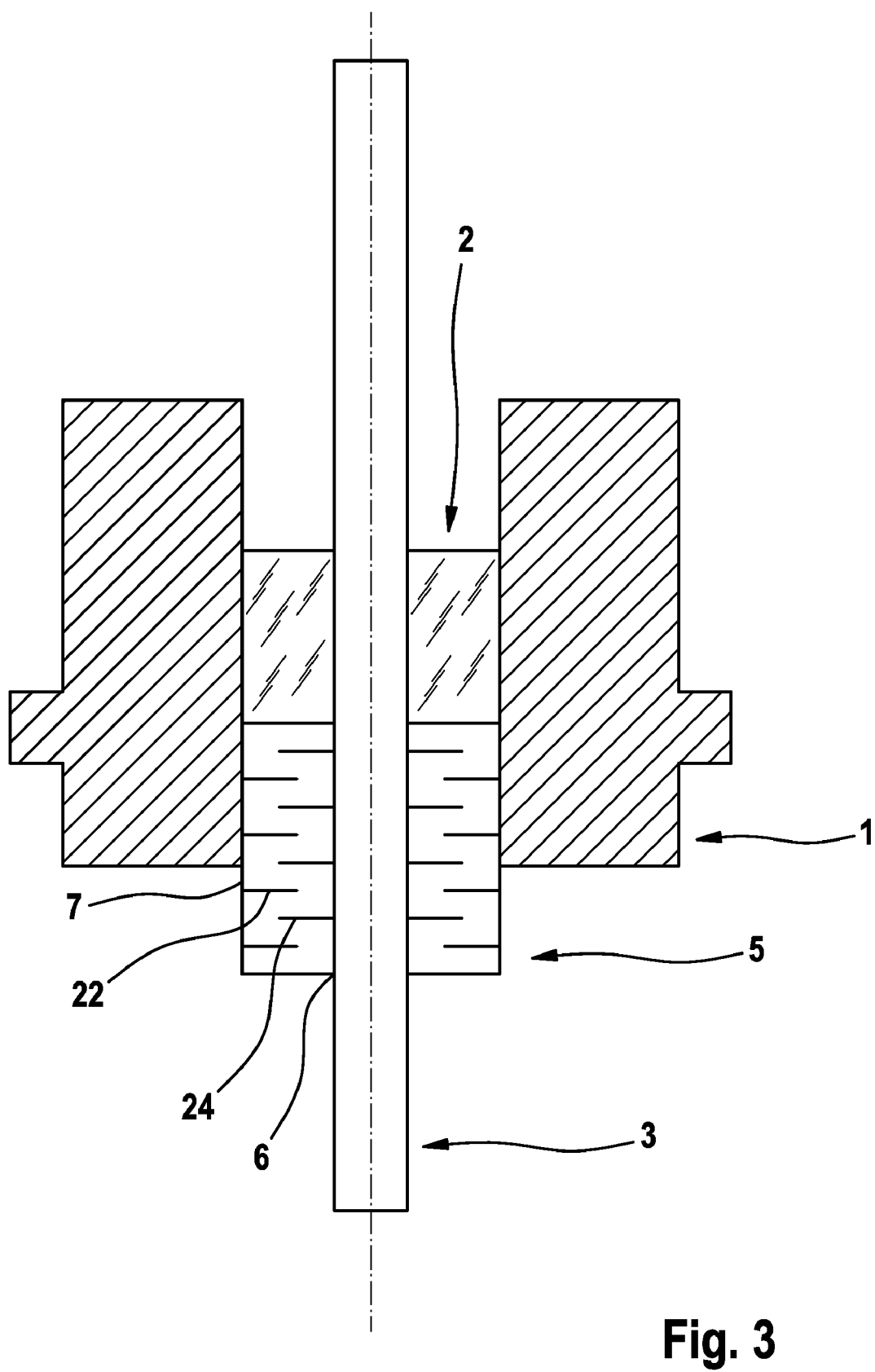
FIG. 3: shows an embodiment of a unipolar filter feedthrough in longitudinal section having integrated capacitor electrodes in the insulation body.

Finally, FIG. 3 shows a variant of a filter feedthrough in which the filter body 5 simultaneously assumes the function of the insulation body, i.e., on one hand it is used as a hold for the terminal pin 3 and on the other hand delimits the cavity which is filled with glass solder 2 together with the flange 1 and the terminal pin 3. FIG. 3 shows how a filter body 5 may also act as an insulation body in the meaning of the present invention. In this meaning, the ceramic bodies 4 according to the embodiment variations 1a through 1f or 2b, 2c, 2e, 2f, 2h, and 2i may also be implemented as filter bodies.

As may be inferred from FIG. 3, a filter body 5 differs from a purely ceramic body in that the filter body 5 has electrically conductive capacitor electrode disks 22 and 27, which are alternately each electrically connected to the terminal pin 3 and to the flange 1. An insulating material, such as ceramic, which is preferably biocompatible, is located between the capacitor electrode disks.

Figure 4C:
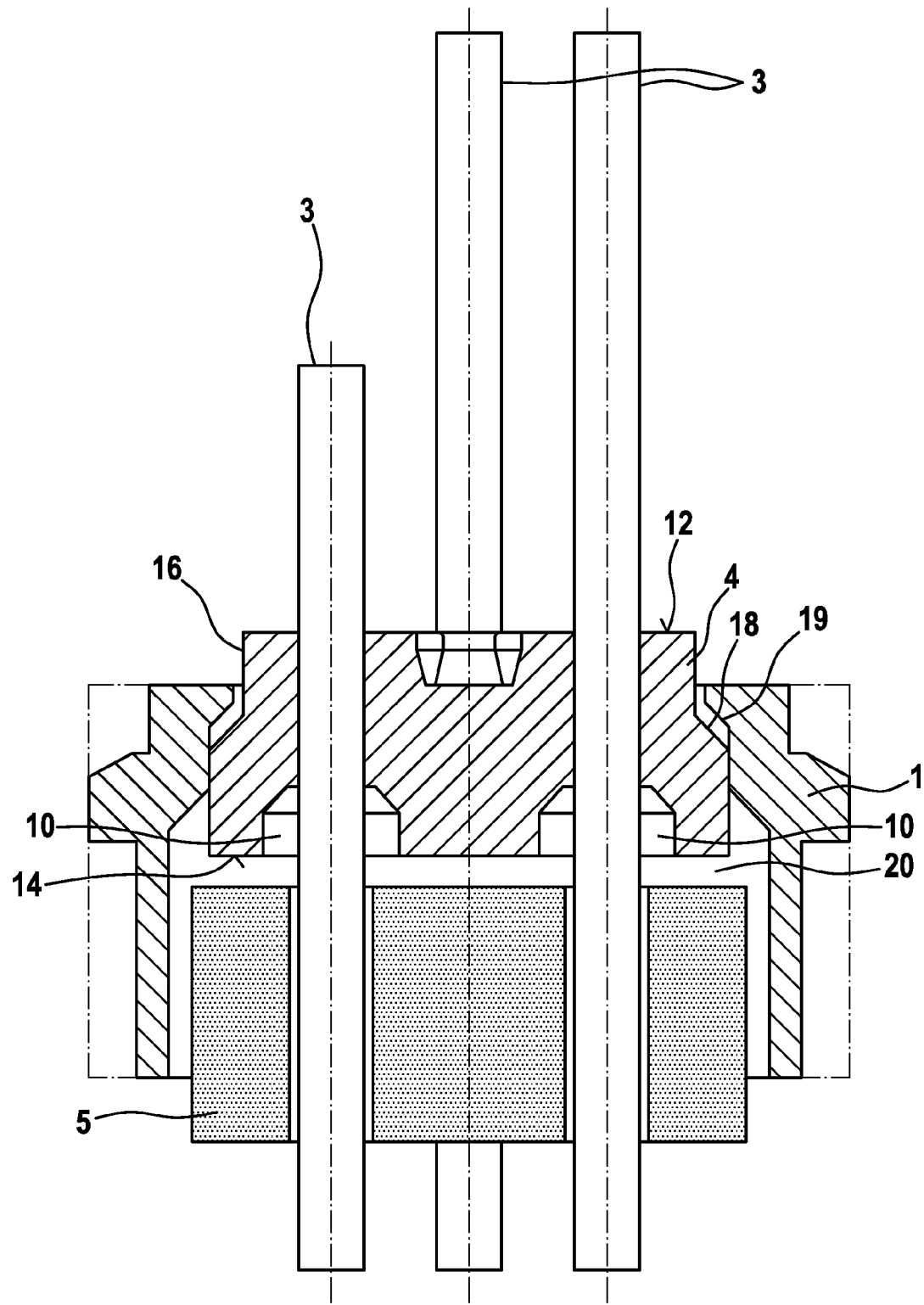
FIG. 4c: show a longitudinal section through the filter feedthrough according to FIGS. 4a and 4b.

Finally, a quadropolar filter feedthrough is shown in FIG. 4. FIGS. 4a and 4b show the filter feedthrough in a top view and a side view. FIG. 4c is a longitudinal section AA through the filter feedthrough (see FIG. 4a).

The filter feedthrough from FIG. 4 has four terminal pins 3, which project through corresponding through openings in an insulation body, which is implemented as a ceramic body 4.

The ceramic body 4 preferably comprises $Al_2O_3$. The terminal pins 3 preferably comprise a platinum-iridium alloy PtIr 90/10. The through openings in the ceramic body 4, through which the terminal pins 3 project, are each expanded at a longitudinal end in such a way that a cavity in the form of an annular space 10 arises between the particular terminal pin 3 and the ceramic body 4. These annular spaces 10 are situated on an internal front face 14 of the ceramic body 4. The annular spaces 10 are filled with glass or glass-ceramic solder 5 in the finished, mounted feedthrough, which is not shown in FIG. 4.

The ceramic body 4 is enclosed by a flange 1, which preferably comprises titanium. Furthermore, it is to be noted in regard to the design of the ceramic body 4 according to the exemplary embodiment variation shown in FIG. 4 that the ceramic body 4 has a cross-section, running perpendicularly to the longitudinal direction of the terminal pin 3, having a circular circumference. The four terminal pins 3 are parallel to one another and are distributed uniformly on a circular arc, which is concentric to the remaining ceramic body 4, in relation to the cross-section of the ceramic body 4.

Two of the terminal pins 3 are shorter than the two other terminal pins 3, to make contacting corresponding terminals in a header of an implant easier.

It may be seen in the longitudinal section through the ceramic body 4 shown in FIG. 4c that the ceramic body 4 has a shoulder 18 in its external peripheral surface 16, so that a conical mantle surface results, which corresponds to a corresponding shoulder 19 in the flange 1.

The flange 1 extends beyond the inner front face 14 of the ceramic body 4 in the longitudinal direction of the filter feedthrough, so that the flange 1 encloses a free space 20 on the interior of the filter feedthrough in which a filter body 5 is inserted. The filter body 5 is optional and may also be left out in the case in which a simple feedthrough and not a filter feedthrough is required.

A typical filter body 5 has multiple electrodes running parallel to one another and transversely to the longitudinal direction of the terminal pin 3, of which each second electrode 22 extends up into an external peripheral surface of the filter body 5, while the electrodes 24 lying between them extend up to a particular through hole for a particular terminal pin 3; see FIG. 3.

A ground pin 26 is situated on the exterior of the flange 1, which provides a possibility of electrically contacting the implant housing with the control electronics securely.

Figure 5:
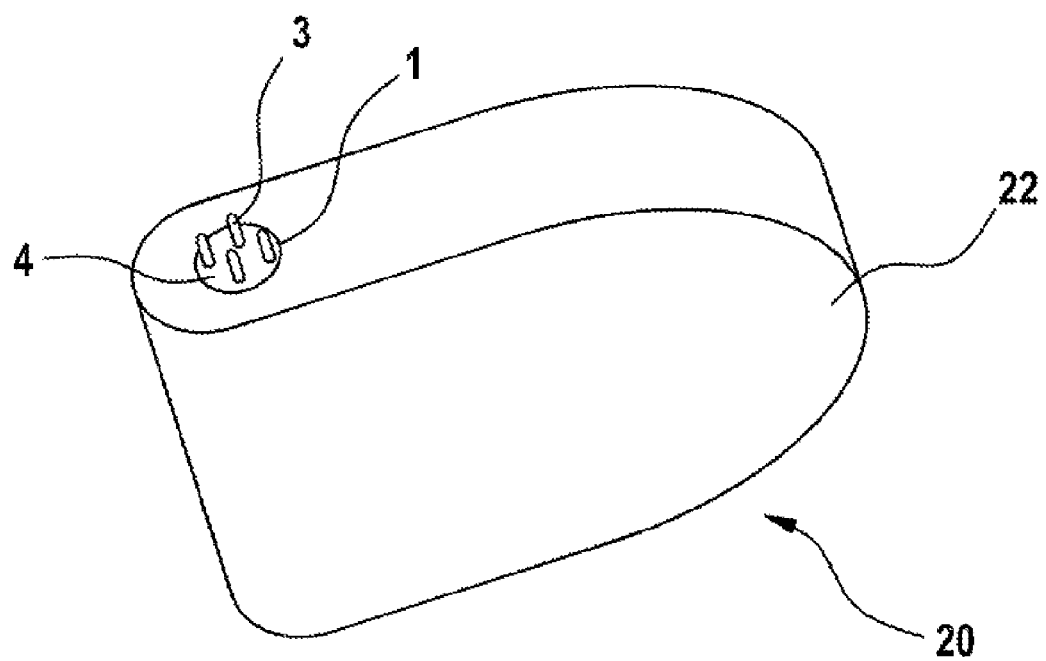
FIG. 5: shows a cardiac pacemaker having a feedthrough according to the present invention.

Finally, FIG. 5 shows an example of a cardiac pacemaker 20 whose metallic housing has already been closed using a filter feedthrough of the type shown in FIGS. 4a-c. For the sake of simplicity, the typical heading of a cardiac pacemaker is not shown in FIG. 5, in which the terminal sockets for the electrode lines are located. The electrical contacts of these terminal sockets are electrically connected to the pins 3 of the filter feedthrough in the finished cardiac pacemaker. The filter feedthrough—more precisely its flange 1—is connected hermetically sealed to the housing 22 of the cardiac pacemaker 20, preferably by welding. Therefore, it is advantageous if the flange 1 of the filter feedthrough comprises the same metal as the housing 28 of the cardiac pacemaker 20.

It is to be noted that the variations shown in FIGS. 1a through 2o may also occur in further combinations, which are not shown here.

What is claimed is:

1. An electrical feedthrough for insertion into an opening of an implantable electrical treatment device comprising:
   at least one terminal pin (3) that is electrically conductive;
   an insulation body (4; 5) which is electrically insulating, through which the at least one terminal pin (3) passes;
   a solder (2) that is made of glass or glass ceramic;
   a flange (1);
   wherein said solder (2) simultaneously connects said flange (1), said at least one terminal pin (3), said insulation body (4;5) to one another;
   wherein said at least one terminal pin (3) is indirectly connected and hermetically sealed to said insulation body (4; 5) with said solder (2) that is made of glass or glass ceramic;
   wherein said at least one terminal pin (3) is indirectly connected and hermetically sealed to said flange (1) with said solder (2) that is made of glass or glass ceramic;
   wherein said flange (1) is situated against said insulation body (4; 5) but does not directly attach with said insulation body (4; 5) and wherein said flange (1) is indirectly hermetically sealed to said insulation body (4; 5) with said solder (2) that is made of glass or glass ceramic; and,
   wherein said insulation body (4; 5) and said flange (1) do not melt into one another or wet one another.

2. The feedthrough according to claim 1, wherein said insulation body (4;5) is a ceramic body comprising $Al_2O_3$ or comprises ceramic material.

3. The feedthrough according to claim 1, wherein said at least one terminal pin (3) comprises metal.

4. The feedthrough according to claim 3, wherein said metal of said at least one terminal pin (3) is a metal that comprises any combination or subset of platinum, niobium, tantalum, and titanium or an alloy of these metals.

5. The feedthrough according to claim 4, wherein said metal of said at least one terminal pin (3) is a platinum-iridium alloy.

6. The feedthrough according to claim 1, wherein said insulation body (4; 5) has through openings, into each of which a terminal pin selected from said at least one terminal pin (3) is inserted and connected and hermetically sealed to said insulation body (4; 5) with said solder (2) that is made of glass or glass ceramic.

7. The feedthrough according to claim 6, wherein said solder (2) made of glass or glass-ceramic is biocompatible.

8. The feedthrough according to claim 6, wherein said through openings have a diameter on at least one longitudinal end which is greater than a diameter of said at least one terminal pin (3), so that an annular space or a cavity (10) comprises said solder (2).

9. The feedthrough according to claim 8, wherein said feedthrough has multiple terminal pins selected from said at least one terminal pin (3) and a corresponding number of through openings, which are each radially expanded on only one longitudinal end in such a way that corresponding annular spaces (10) or cavities from said at least one terminal pin (3) to said at least one terminal pin (3) result on a same front face of said insulation body (4; 5).

10. The feedthrough according to claim 9, wherein said feedthrough has multiple terminal pins selected from said at least one terminal pin (3) and a corresponding number of through openings, which are each radially expanded on only one longitudinal end in such a way that at least one shared cavity of two or more of said at least one terminal pin (3) results on a front face of said insulation body (4; 5).

11. The feedthrough according to claim 10, wherein said feedthrough has two or more terminal pins selected from said at least one terminal pin (3) of different lengths.

12. The feedthrough according to claim 1, wherein said feedthrough has two or more terminal pins selected from said at least one terminal pin (3) running parallel to one another.

13. The feedthrough according to claim 12, wherein said at least one terminal pin (3) are distributed uniformly on a circular arc running concentrically to said insulation body (4; 5).

14. The feedthrough according to claim 13, wherein said at least one terminal pin (3) are distributed uniformly on a straight line or multiple straight lines running parallel to one another.

15. The feedthrough according to claim 1, wherein a cross-sectional surface of said insulation body (4; 5) running perpendicularly to a longitudinal direction of said at least one terminal pin (3) is round and circular.

16. The feedthrough according to claim 1, wherein said insulation body (4; 5) is enclosed in a lateral direction in relation to a longitudinal direction of said at least one terminal pin (3) by a flange (1) that is formed by a sleeve-like metallic flange.

17. The feedthrough according to claim 16, wherein said flange (1) is metallically conductive.

18. The feedthrough according to claim 17, wherein said flange (1) comprises a metal, which corresponds to a metal of a housing of a treatment device for which said feedthrough is provided.

19. The feedthrough according to claim 17, wherein said flange (1) comprises sintered material, which contains numerous pores as a result of a sintering process.

20. The feedthrough according to claim 17, wherein said feedthrough is implemented as a filter feedthrough and carries a filter body (5), which has capacitor electrode disks (22, 27), which are alternately electrically connected to said flange (1) and said at least one terminal pin (3).

21. The feedthrough according to one of claim 1, wherein said insulation body (4; 5) has a peripheral shoulder (18) in an external peripheral surface.

22. The feedthrough according to claim 21, wherein said peripheral shoulder (18) is implemented as inclined.

23. The feedthrough according to claim 22, wherein said peripheral shoulder (18) which is inclined of said insulation body (4; 5) finds a corresponding shoulder (19) on said flange (1) as a centering aid.

24. The feedthrough according to claim 23, wherein said shoulder (19) on said flange (1) used as a centering aid for said insulation body (4; 5) is implemented as inclined, matching said peripheral shoulder (18) which is inclined of said insulation body (4; 5).

25. The feedthrough according to claim 1 further coupled with an implantable electrotherapy device, or a cardiac pacemaker or cardioverter/defibrillator.

* * * * *